United States Patent
Wu et al.

(10) Patent No.: US 8,130,378 B2
(45) Date of Patent: Mar. 6, 2012

(54) PHASE RETARDANCE INSPECTION INSTRUMENT

(75) Inventors: Chun-I Wu, Tainan (TW); Kai-Ping Chuang, Pingtung County (TW); Wan-Yi Lin, Yunlin County (TW); Yi-Chen Hsieh, Changhua County (TW); Fu-Shiang Yang, Hsinchu County (TW)

(73) Assignee: Industrial Technology Research Institute, Hsin-Chu (TW)

( * ) Notice: Subject to any disclaimer, the term of this patent is extended or adjusted under 35 U.S.C. 154(b) by 472 days.

(21) Appl. No.: 12/367,157

(22) Filed: Feb. 6, 2009

(65) Prior Publication Data

US 2010/0118293 A1    May 13, 2010

(30) Foreign Application Priority Data

Nov. 11, 2008  (TW) ................................ 97143455 A

(51) Int. Cl.
*G01J 4/00* (2006.01)
(52) U.S. Cl. ........................................ 356/364; 356/369
(58) Field of Classification Search .................... None
See application file for complete search history.

(56) References Cited

U.S. PATENT DOCUMENTS

| | | | | |
|---|---|---|---|---|
| 5,373,359 | A * | 12/1994 | Woollam et al. | 356/369 |
| 5,521,705 | A | 5/1996 | Oldenbourg | |
| 6,219,139 | B1 | 4/2001 | Lesniak | |
| 6,961,123 | B1 * | 11/2005 | Wang et al. | 356/364 |
| 7,218,436 | B2 * | 5/2007 | Yao | 356/368 |
| 2007/0146632 | A1 * | 6/2007 | Chipman | 351/205 |
| 2010/0149533 | A1 * | 6/2010 | Fest | 356/367 |

* cited by examiner

*Primary Examiner* — Gregory J Toatley
*Assistant Examiner* — Juan D Valentin
(74) *Attorney, Agent, or Firm* — Morris Manning & Martin LLP; Tim Tingkang Xia, Esq.

(57) ABSTRACT

A phase retardance inspection instrument, comprising: a light source module for generating a single-wavelength light beam; a circularly polarized light generating module, comprising a polarizer and a first phase retarder, for receiving the single-wavelength light beam as it is guided to pass through the polarizer and the first phase retarder in order; and a detecting module, comprising a second phase retarder, a polarizing beam splitter, a first image sensor and a second image sensor, for receiving and guiding a circularly polarized light beam to travel through the second phase retarder and the polarizing beam splitter in order after it passes through a substrate under inspection, wherein the polarizing beam splitter splits an elliptically polarized light beam into intensity vector components of a left-hand circularly polarized light beam and a right-hand circularly polarized light beam, which are to be emitted into the first image sensor and the second image sensor, respectively.

65 Claims, 3 Drawing Sheets

PHASE RETARDANCE INSPECTION INSTRUMENT

CROSS-REFERENCE TO RELATED APPLICATIONS

This non-provisional application claims priority under 35 U.S.C. §119(a) on Patent Application No. 097143455 filed in Taiwan on Nov. 11, 2008, the entire contents of which are hereby incorporated by reference.

BACKGROUND OF THE INVENTION

1. Field of the Invention

The present invention generally relates to a phase retardance inspection instrument.

2. Description of the Prior Art

In recent years, the flexible electronics and display related technology has attracted tremendous attention. However, the stress distribution is an important issue due to the use of flexible materials (such as the plastic substrate) as a substrate. Since the substrate is often used when it is warped, cracks of the substrate or the connecting wires due to stress occur to cause damage to the devices. On the other hand, when the plastic substrate that is flexible is used, stress generated during manufacturing processing also causes warping of the display to damage the devices.

Conventionally, the stress of a thin film is inspected by measuring the curvature variation of a glass or silicon substrate before and after it is coated to calculate the stress value. However, when a flexible plastic substrate is used, conventional curvature measurement cannot be used and real-time measurement cannot be achieved for stress monitoring since the curvature variation is too large. Moreover, since the flexible plastic substrate is formed of polymer with birefringence, such as poly(ethylene terephthalate) (PET) and poly(ethylene naphthalene-2,6-dicarboxylate) (PEN), the stress generated during thin film processing causes the change of birefringence, and the change of phase retardance.

Conventional polarization inspection is performed by rotating polarizing elements or a plurality of polarizing elements to acquire the polarization mode variation. For example, U.S. Pat. No. 6,219,139 "Full field photoelastic stress analysis" filed by Stress Photonics Inc. uses two neutral beam splitters, two polarizing beam splitters, a plurality of polarizing elements, and four image sensors to construct a full field phase retardance stress measurement device.

In U.S. Pat. No. 5,521,705 "Polarized light microscopy" filed by Rudolf Oldenbourg and Guang Mei, a liquid crystal phase compensator is used to replace the conventional phase compensator, wherein the input voltage is adjusted to control the phase retardance value of the compensator to obtain different polarization modes. U.S. Pat. No. 5,521,705 can do without any rotating polarizing element, but the liquid crystal phase compensator does not provide real-time adjustment.

SUMMARY OF THE INVENTION

The present invention provides a phase retardance inspection instrument for inspecting a transparent substrate, comprising: a light source module for generating a single-wavelength light beam; a circularly polarized light generating module comprising a polarizer and a first phase retarder, wherein the single-wavelength light beam passes through the polarizer and the first phase retarder in order after it is emitted into the circularly polarized light generating module; and a detecting module comprising a second phase retarder, a polarizing beam splitter, a first image sensor and a second image sensor, wherein an elliptically polarized light beam passes through the second phase retarder and the polarizing beam splitter in order after a circularly polarized light beam passes through a substrate under inspection and enters the detecting module, and wherein the polarizing beam splitter splits the elliptically polarized light beam into intensity vector components of a left-hand circularly polarized light beam and a right-hand circularly polarized light beam, which are to be emitted into the first image sensor and the second image sensor, respectively.

The present invention further provides a phase retardance inspection instrument for inspecting a reflective substrate, comprising: a light source module for generating a single-wavelength light beam; a circularly polarized light generating module comprising a polarizer and a first phase retarder, wherein the single-wavelength light beam passes through the polarizer and the first phase retarder in order after it is emitted into the circularly polarized light generating module; a neutral beam splitting unit for guiding a circularly polarized light beam that passes through the circularly polarized light generating module into the reflective substrate; and a detecting module comprising a second phase retarder, a polarizing beam splitter, a first image sensor and a second image sensor, wherein an elliptically polarized light beam passes through the second phase retarder and the polarizing beam splitter in order after the circularly polarized light beam is reflected by the reflective substrate under inspection and enters the detecting module, and wherein the polarizing beam splitter splits the elliptically polarized light beam into intensity vector components of a left-hand circularly polarized light beam and a right-hand circularly polarized light beam, which are to be emitted into the first image sensor and the second image sensor, respectively.

BRIEF DESCRIPTION OF THE DRAWINGS

The objects and spirits of various embodiments of the present invention will be readily understood by the accompanying drawings and detailed descriptions, wherein.

DETAILED DESCRIPTION OF THE PREFERRED EMBODIMENT

The present invention can be exemplified but not limited by the embodiments as described hereinafter.

Figure 1:
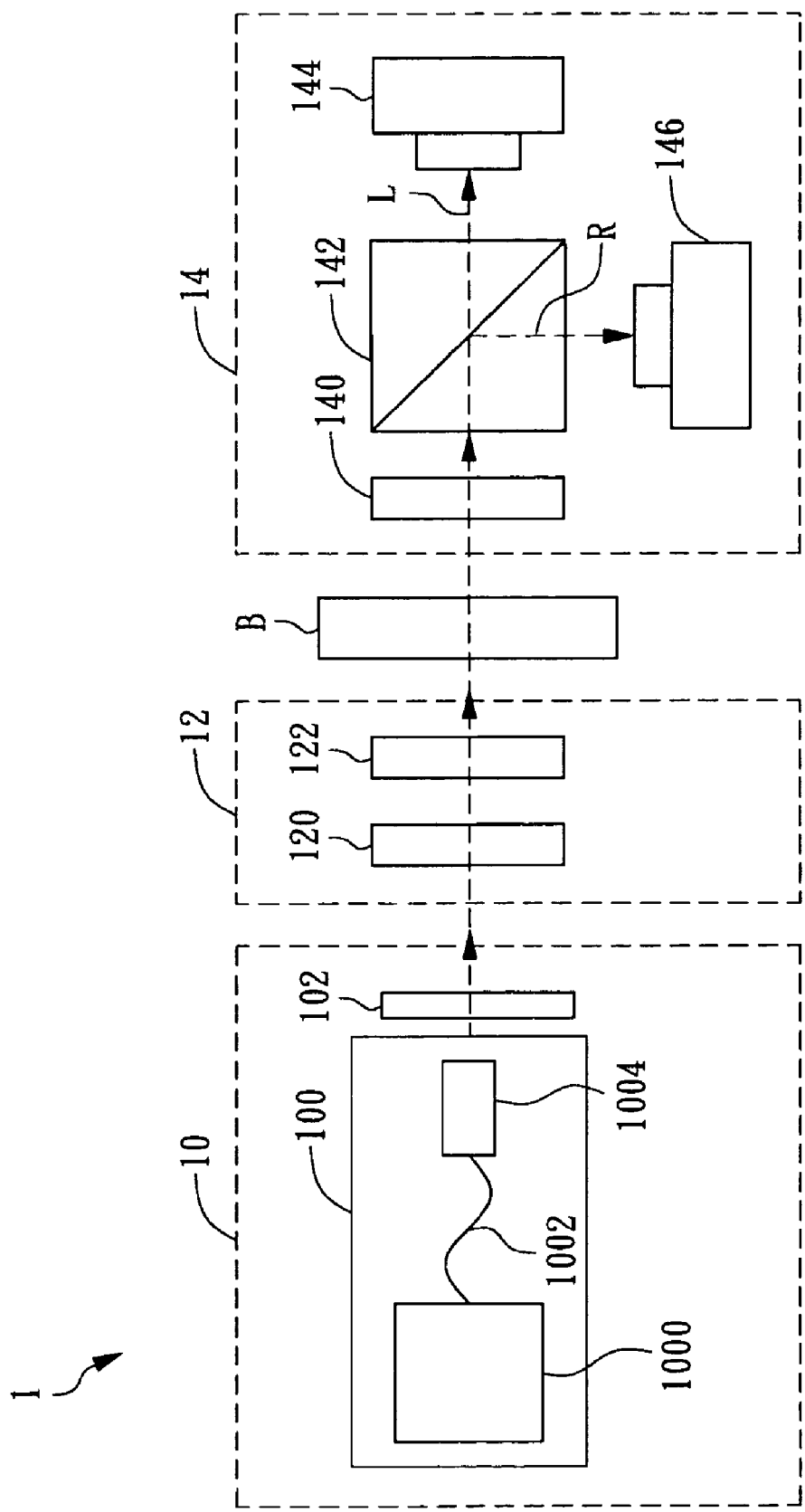
FIG. 1 is a schematic diagram of a phase retardance inspection instrument according to one embodiment of the present invention.

Please refer to FIG. 1, which is a schematic diagram of a phase retardance inspection instrument according to one embodiment of the present invention. In the present embodiment, the phase retardance inspection instrument 1 comprises a light source module 10, a circularly polarized light generating module 12 and a detecting module 14.

The light source module 10 generates a single-wavelength light beam, preferably, a collimated light beam. Certainly, a multi-wavelength light source and a single-wavelength filter can be used to emit single-wavelength light. As shown in FIG. 1, the light source module 10 comprises a multi-wavelength light emitter 100 and a single-wavelength filter 102. The multi-wavelength light emitter 100 emits a multi-wavelength collimated light beam. The single-wavelength filter 102 filters the multi-wavelength collimated light beam to generate a single-wavelength collimated light beam. The multi-wavelength light emitter 100 comprises a multi-wavelength light source 1000, a collimating lens 1004 and a light guide 1002 connected to the multi-wavelength light source 1000 and the collimating lens 1004, respectively. The light emitted from the multi-wavelength light source 1000 is guided by the light guide 1002 into the collimating lens 1004 so that it is to be collimated and emitted. The multi-wavelength light source 1000 is, for example, a halogen lamp, a flash lighter, a LED lamp, a multi-wavelength laser or a multi-wavelength vapor lamp. The light emitted from the multi-wavelength light source 1000 is, for example, visible light with a wavelength in a range from 380 nm to 750 nm or infrared light with a wavelength larger than 750 nm.

The circularly polarized light generating module 12 comprises a polarizer 120 and a first phase retarder 122. The single-wavelength collimated light beam emitted from the light source module 10 passes through the polarizer 120 and the first phase retarder 122 in order to generate circularly polarized light after it is emitted into the circularly polarized light generating module 12.

Then, the circularly polarized light passes through a substrate B under inspection. The substrate B is a transparent substrate comprising, for example, plastic, glass or silicon. Since the substrate B exhibits non-uniform stress distribution or warping (when the substrate is flexible) during fabrication, the circularly polarized light is converted into an elliptically polarized light beam with phase retardance after it passes through the substrate.

The detecting module 14 comprises a second phase retarder 140, a polarizing beam splitter 142, a first image sensor 144 and a second image sensor 146. The elliptically polarized light beam passes through the second phase retarder 140 and the polarizing beam splitter 142 in order after the circularly polarized light beam passes through a substrate B under inspection and enters the detecting module 14. The polarizing beam splitter 142 splits the elliptically polarized light beam into intensity vector components of a left-hand circularly polarized light beam L and a right-hand circularly polarized light beam R, which are to be emitted into the first image sensor 144 and the second image sensor 146, respectively, to detect the intensity vector components of the left-hand circularly polarized light beam L and the right-hand circularly polarized light beam R.

Figure 2:
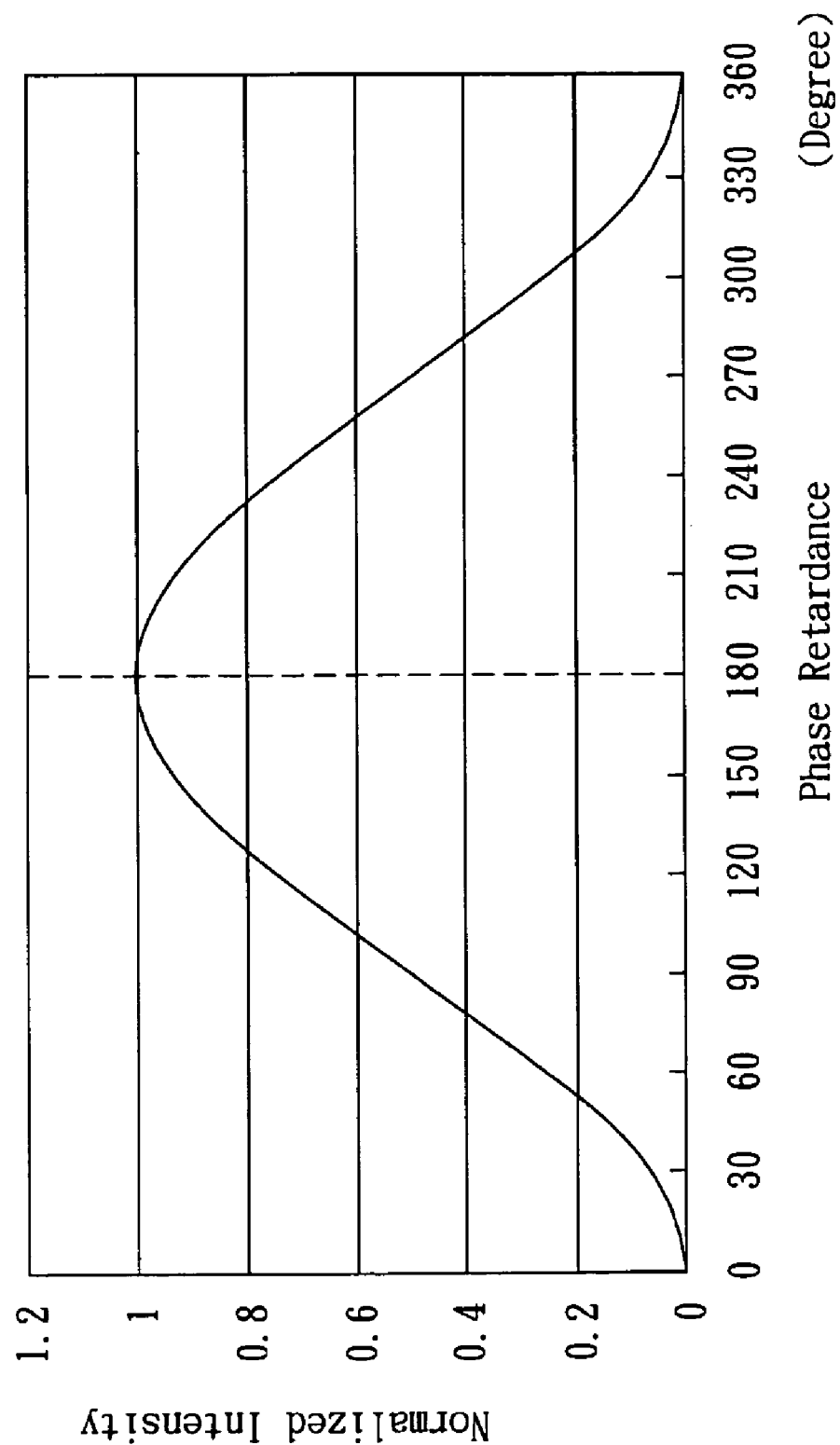
FIG. 2 is a relation between the image intensity and the phase retardance with respect to the the intensity vector components of the left-hand circularly polarized light beam.

If the intensity vector component of the left-hand circularly polarized light beam L is P and the intensity vector component of the right-hand circularly polarized light beam R is S, we obtain normalized intensities by:

$$I_P = P/(P+S) = \sin^2(\pi R/\lambda)$$

$$I_S = S/(P+S) = \cos^2(\pi R/\lambda)$$

Wherein $I_P$ is the intensity vector component of the left-hand circularly polarized light beam, $I_S$ is the intensity vector component of the right-hand circularly polarized light beam, $\lambda$ is the monochromatic wavelength of light passing through the substrate under inspection, and R is the phase retardance. FIG. 2 is a relation between the image intensity and the phase retardance with respect to the intensity vector components of the left-hand circularly polarized light beam.

Generally, the phase retardance R can be calculated from $I_P$, and can be calculated from $I_S$ when the intensity of P is weak. Since the intensity of S is strong and the signal-to-noise ration is high, the calculation result is more precise. Theoretically, the phase retardance R from $I_P$ is identical to that from $I_S$. However, since the polarizing beam splitter may not equally splits light and the intensity responses of the first image sensor and the second image sensor may not be identical, the calculated phase retardances R may not be identical, which can be corrected by measuring the intensity of P and the intensity of S with respect to the air with zero phase retardance.

As the phase retardance R has been calculated, the stress a in the irradiated substrate area can be calculated using the formula:

$$R = C \cdot \sigma \cdot d$$

Wherein R is the phase retardance, C is the stress optic constant (which can be acquired from the look-up table or from measurement) and d is the thickness of the substrate under inspection.

Figure 3:
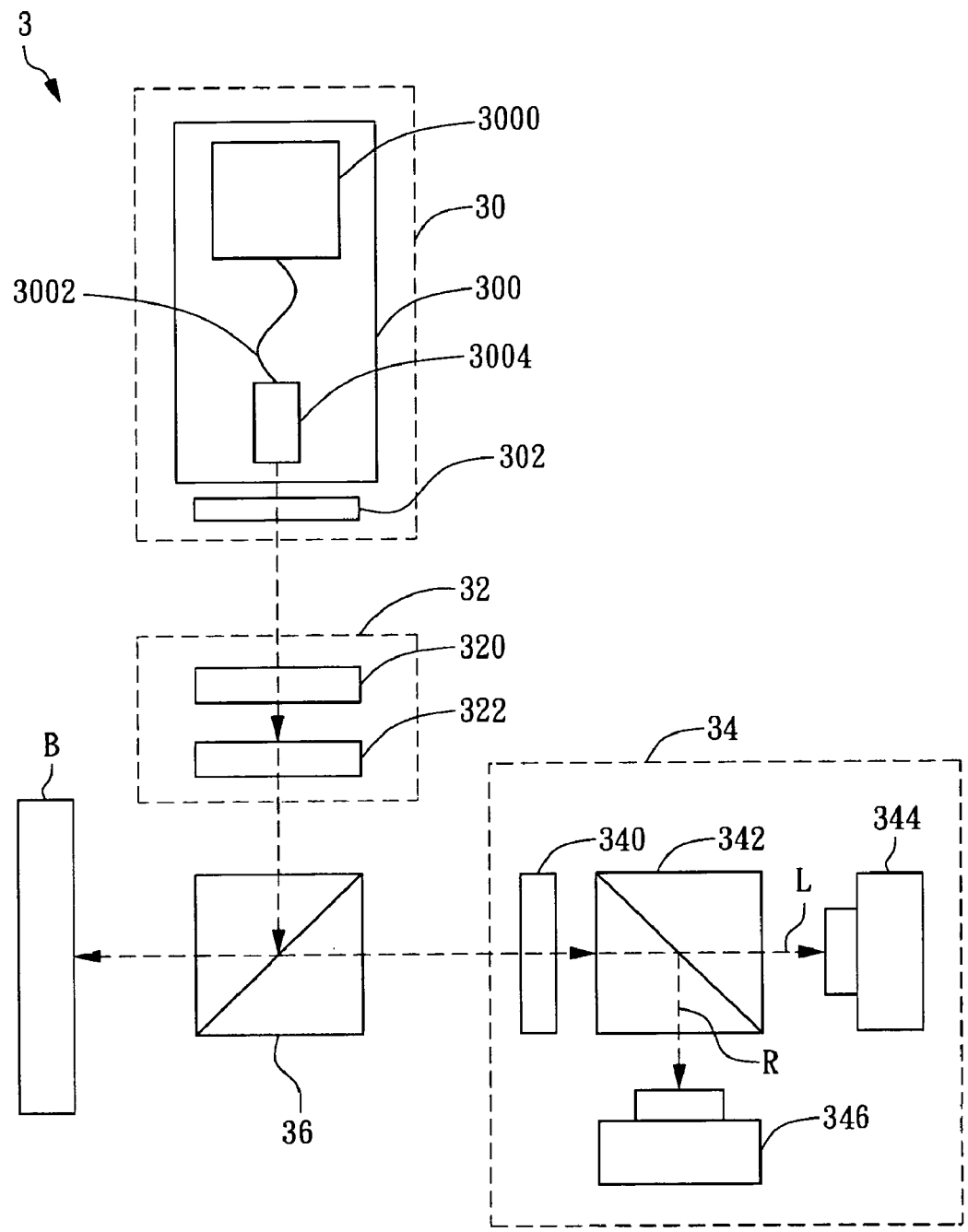
FIG. 3 is a schematic diagram of a phase retardance inspection instrument according to another embodiment of the present invention.

Please refer to FIG. 3, which is a schematic diagram of a phase retardance inspection instrument according to another embodiment of the present invention. The elements of the phase retardance inspection instrument 3 are similar to the phase retardance inspection instrument 1 in FIG. 1 to comprises a light source module 30, a circularly polarized light generating module 32 and a detecting module 34, except that the phase retardance inspection instrument 3 further comprise a neutral beam splitting unit 36 since the substrate is reflective.

As stated in the previous embodiment, the light source module 30 generates a single-wavelength light beam, preferably, a collimated light beam. Certainly, a multi-wavelength light source and a single-wavelength filter can be used to emit single-wavelength light. As shown in FIG. 3, the light source module 30 comprises a multi-wavelength light emitter 300 and a single-wavelength filter 302. The multi-wavelength light emitter 300 emits a multi-wavelength collimated light beam. The single-wavelength filter 302 filters the multi-wavelength collimated light beam to generate a single-wavelength collimated light beam. The multi-wavelength light emitter 300 comprises a multi-wavelength light source 3000, a collimating lens 3004 and a light guide 3002 connected to the multi-wavelength light source 3000 and the collimating lens 3004, respectively. The light emitted from the multi-wavelength light source 3000 is guided by the light guide 3002 into the collimating lens 3004 so that it is to be collimated and emitted. The multi-wavelength light source 3000 is, for example, a halogen lamp, a flash lighter, a LED lamp, a multi-wavelength laser or a multi-wavelength vapor lamp. The light emitted from the multi-wavelength light source 3000 is, for example, visible light with a wavelength in a range from 380 nm to 750 nm or infrared light with a wavelength larger than 750 nm.

The circularly polarized light generating module 32 comprises a polarizer 320 and a first phase retarder 322. The single-wavelength collimated light beam emitted from the light source module 30 passes through the polarizer 320 and the first phase retarder 322 in order to generate circularly polarized light after it is emitted into the circularly polarized light generating module 32.

Then, the circularly polarized light passes through the neutral beam splitting unit 36 (for example, a neutral beam splitter) and is reflected to a substrate B under inspection. The substrate B is a reflective substrate comprising, for example, plastic or silicon. Since the substrate B exhibits non-uniform stress distribution or warping (when the substrate is flexible) during fabrication, the circularly polarized light is converted into an elliptically polarized light beam with phase retardance after it passes through the substrate. Then, the elliptically polarized light beam is reflected by the substrate B to the neutral beam splitting unit 36 and is emitted into the detecting module 34.

The detecting module 34 comprises a second phase retarder 340, a polarizing beam splitter 342, a first image sensor 344 and a second image sensor 346. The elliptically polarized light beam passes through the second phase retarder 340 and the polarizing beam splitter 342 in order after the circularly polarized light beam is reflected by a substrate B under inspection and enters the detecting module 34. The polarizing beam splitter 342 splits the elliptically polarized light beam into intensity vector components of a left-hand circularly polarized light beam L and a right-hand circularly polarized light beam R, which are to be emitted into the first image sensor 344 and the second image sensor 346, respectively, to detect the intensity vector components of the left-hand circularly polarized light beam L and the right-hand circularly polarized light beam R.

When the intensity is measured, the phase retardance R is obtained as stated above. For the reflective phase retardance inspection instrument, as the phase retardance R has been calculated, the stress a in the irradiated substrate area can be calculated using the formula:

$$R = C \cdot \sigma \cdot 2d$$

Wherein R is the phase retardance, C is the stress optic constant (which can be acquired from the look-up table or from measurement) and d is the thickness of the substrate under inspection.

Therefore, the present invention provides phase retardance distribution inspecting and improves inspection accuracy by adjusting the intensity vector components of the left-hand circularly polarized light beam or the right-hand circularly polarized light beam. Moreover, the stress of the substrate can be calculated after the phase retardance value is obtained.

In the present invention, the polarizer is a Glan-Thomson polarizer or a thin film polarizer; the first phase retarder and the second phase retarder are crystal phase plates or prismatic phase plates; the polarizing beam splitter is a crystal, prismatic or thin film polarizing beam splitter; and the first image sensor and the second image sensor are charge-coupled device (CCD) image sensors, complementary metal-oxide-semiconductor (CMOS) image sensors, 2-D LED array image sensors or photo-multiplier tubes (PMT's). Meanwhile, the light beam in the present invention is not limited to the collimated light beam.

Accordingly, the present invention provides a phase retardance inspection instrument capable of inspecting a stress value on a substrate under inspection and improving inspection accuracy by adjusting the intensity vector components of the left-hand circularly polarized light beam or the right-hand circularly polarized light beam. Moreover, the stress of the substrate can be calculated after the phase retardance value is obtained. Therefore, the present invention is useful, novel and non-obvious.

Although this invention has been disclosed and illustrated with reference to particular embodiments, the principles involved are susceptible for use in numerous other embodiments that will be apparent to persons skilled in the art. This invention is, therefore, to be limited only as indicated by the scope of the appended claims.

What is claimed is:

1. A phase retardance inspection instrument for inspecting a transparent substrate, comprising:
    a light source module for generating a single-wavelength light beam;
    a circularly polarized light generating module comprising a polarizer and a first phase retarder, wherein the single-wavelength light beam passes through the polarizer and the first phase retarder sequentially so as to generate a circularly polarized light after it is emitted into the circularly polarized light generating module; and
    a detecting module comprising a second phase retarder, a polarizing beam splitter, a first image sensor and a second image sensor, wherein an elliptically polarized light beam is generated by passing the circularly polarized light beam through the transparent substrate under inspection, the elliptically polarized light beam then passes through the second phase retarder and the polarizing beam splitter sequentially and enters the detecting module, and wherein the polarizing beam splitter splits the elliptically polarized light beam into intensity vector components of a left-hand circularly polarized light beam and a right-hand circularly polarized light beam, which are to be emitted into the first image sensor and the second image sensor, respectively.

2. The phase retardance inspection instrument as recited in claim 1, wherein the light source module comprises a multi-wavelength light emitter for emitting a multi-wavelength light beam and a single-wavelength filter for filtering the multi-wavelength light beam to generate a single-wavelength light beam.

3. The phase retardance inspection instrument as recited in claim 2, wherein the multi-wavelength light emitter comprises a multi-wavelength light source, a collimating lens, and a light guide connected to the multi-wavelength light source and the collimating lens, respectively.

4. The phase retardance inspection instrument as recited in claim 3, wherein the multi-wavelength light source emits visible light.

5. The phase retardance inspection instrument as recited in claim 3, wherein the multi-wavelength light source emits white light.

6. The phase retardance inspection instrument as recited in claim 3, wherein the multi-wavelength light source emits flash light.

7. The phase retardance inspection instrument as recited in claim 3, wherein the multi-wavelength light source emits multi-wavelength laser light.

8. The phase retardance inspection instrument as recited in claim 3, wherein the multi-wavelength light source is a multi-wavelength vapor lamp.

9. The phase retardance inspection instrument as recited in claim 3, wherein the multi-wavelength light source is a multi-wavelength light emitting diode (LED).

10. The phase retardance inspection instrument as recited in claim 3, wherein the multi-wavelength light source is a multi-wavelength fluorescent lamp.

11. The phase retardance inspection instrument as recited in claim 1, wherein the light source module emits single-wavelength collimated light.

12. The phase retardance inspection instrument as recited in claim 11, wherein the wavelength of the single-wavelength collimated light is larger than the wavelength of visible light.

13. The phase retardance inspection instrument as recited in claim 11, wherein the single-wavelength collimated light is infrared light.

14. The phase retardance inspection instrument as recited in claim 1, wherein the substrate is flexible.

15. The phase retardance inspection instrument as recited in claim 1, wherein the substrate is plastic.

16. The phase retardance inspection instrument as recited in claim 1, wherein the polarizer is a prismatic polarizer.

17. The phase retardance inspection instrument as recited in claim 1, wherein the polarizer is a thin film polarizer.

18. The phase retardance inspection instrument as recited in claim 1, wherein the first phase retarder is a crystal phase plate.

19. The phase retardance inspection instrument as recited in claim 1, wherein the first phase retarder is a prismatic phase plate.

20. The phase retardance inspection instrument as recited in claim 1, wherein the second phase retarder is a crystal phase plate.

21. The phase retardance inspection instrument as recited in claim 1, wherein the second phase retarder is a prismatic phase plate.

22. The phase retardance inspection instrument as recited in claim 1, wherein the polarizing beam splitter is a crystal polarizing beam splitter.

23. The phase retardance inspection instrument as recited in claim 1, wherein the polarizing beam splitter is a prismatic polarizing beam splitter.

24. The phase retardance inspection instrument as recited in claim 1, wherein the polarizing beam splitter is a thin film polarizing beam splitter.

25. The phase retardance inspection instrument as recited in claim 1, wherein the first image sensor is a charge-coupled device (CCD) image sensor.

26. The phase retardance inspection instrument as recited in claim 1, wherein the first image sensor is a complementary metal-oxide-semiconductor (CMOS) image sensor.

27. The phase retardance inspection instrument as recited in claim 1, wherein the first image sensor is a 2-D LED array image sensor.

28. The phase retardance inspection instrument as recited in claim 1, wherein the first image sensor is a photo-multiplier tube (PMT).

29. The phase retardance inspection instrument as recited in claim 1, wherein the second image sensor is a charge-coupled device (CCD) image sensor.

30. The phase retardance inspection instrument as recited in claim 1, wherein the second image sensor is a complementary metal-oxide-semiconductor (CMOS) image sensor.

31. The phase retardance inspection instrument as recited in claim 1, wherein the second image sensor is a 2-D LED array image sensor.

32. The phase retardance inspection instrument as recited in claim 1, wherein the second image sensor is a photo-multiplier tube (PMT).

33. A phase retardance inspection instrument for inspecting a reflective substrate, comprising:
a light source module for generating a single-wavelength light beam;
a circularly polarized light generating module comprising a polarizer and a first phase retarder, wherein the single-wavelength light beam passes through the polarizer and the first phase retarder sequentially so as to generate a circularly polarized light after it is emitted into the circularly polarized light generating module;
a neutral beam splitting unit for guiding a circularly polarized light beam that passes through the circularly polarized light generating module into the reflective substrate; and
a detecting module comprising a second phase retarder, a polarizing beam splitter, a first image sensor and a second image sensor, wherein an elliptically polarized light beam is generated by reflecting the circularly polarized light beam by the reflective substrate under inspection, the elliptically polarized light beam then passes through the neutral beam splitting unit, the second phase retarder and the polarizing beam splitter sequentially and enters the detecting module, and wherein the polarizing beam splitter splits the elliptically polarized light beam into intensity vector components of a left-hand circularly polarized light beam and a right-hand circularly polarized light beam, which are to be emitted into the first image sensor and the second image sensor, respectively.

34. The phase retardance inspection instrument as recited in claim 33, wherein the light source module comprises a multi-wavelength light emitter for emitting a multi-wavelength light beam and a single-wavelength filter for filtering the multi-wavelength light beam to generate a single-wavelength light beam.

35. The phase retardance inspection instrument as recited in claim 34, wherein the multi-wavelength light emitter comprises a multi-wavelength light source, a collimating lens, and a light guide connected to the multi-wavelength light source and the collimating lens, respectively.

36. The phase retardance inspection instrument as recited in claim 35, wherein the multi-wavelength light source emits visible light.

37. The phase retardance inspection instrument as recited in claim 35, wherein the multi-wavelength light source emits white light.

38. The phase retardance inspection instrument as recited in claim 35, wherein the multi-wavelength light source emits flash light.

39. The phase retardance inspection instrument as recited in claim 35, wherein the multi-wavelength light source emits multi-wavelength laser light.

40. The phase retardance inspection instrument as recited in claim 35, wherein the multi-wavelength light source is a multi-wavelength vapor lamp.

41. The phase retardance inspection instrument as recited in claim 35, wherein the multi-wavelength light source is a multi-wavelength light emitting diode (LED).

42. The phase retardance inspection instrument as recited in claim 35, wherein the multi-wavelength light source is a multi-wavelength fluorescent lamp.

43. The phase retardance inspection instrument as recited in claim 33, wherein the light source module emits single-wavelength collimated light.

44. The phase retardance inspection instrument as recited in claim 43, wherein the wavelength of the single-wavelength collimated light is larger than the wavelength of visible light.

45. The phase retardance inspection instrument as recited in claim 43, wherein the single-wavelength collimated light is infrared light.

46. The phase retardance inspection instrument as recited in claim 33, wherein the reflective substrate is flexible.

47. The phase retardance inspection instrument as recited in claim 33, wherein the reflective substrate is plastic.

48. The phase retardance inspection instrument as recited in claim 33, wherein the polarizer is a prismatic polarizer.

49. The phase retardance inspection instrument as recited in claim 33, wherein the polarizer is a thin film polarizer.

50. The phase retardance inspection instrument as recited in claim 33, wherein the first phase retarder is a crystal phase plate.

51. The phase retardance inspection instrument as recited in claim 33, wherein the first phase retarder is a prismatic phase plate.

52. The phase retardance inspection instrument as recited in claim 33, wherein the second phase retarder is a crystal phase plate.

53. The phase retardance inspection instrument as recited in claim 33, wherein the second phase retarder is a prismatic phase plate.

54. The phase retardance inspection instrument as recited in claim 33, wherein the polarizing beam splitter is a crystal polarizing beam splitter.

55. The phase retardance inspection instrument as recited in claim 33, wherein the polarizing beam splitter is a prismatic polarizing beam splitter.

56. The phase retardance inspection instrument as recited in claim 33, wherein the polarizing beam splitter is a thin film polarizing beam splitter.

57. The phase retardance inspection instrument as recited in claim 33, wherein the first image sensor is a charge-coupled device (CCD) image sensor.

58. The phase retardance inspection instrument as recited in claim 33, wherein the first image sensor is a complementary metal-oxide-semiconductor (CMOS) image sensor.

59. The phase retardance inspection instrument as recited in claim 33, wherein the first image sensor is a 2-D LED array image sensor.

60. The phase retardance inspection instrument as recited in claim 33, wherein the first image sensor is a photo-multiplier tube (PMT).

61. The phase retardance inspection instrument as recited in claim 33, wherein the second image sensor is a charge-coupled device (CCD) image sensor.

62. The phase retardance inspection instrument as recited in claim 33, wherein the second image sensor is a complementary metal-oxide-semiconductor (CMOS) image sensor.

63. The phase retardance inspection instrument as recited in claim 33, wherein the second image sensor is a 2-D LED array image sensor.

64. The phase retardance inspection instrument as recited in claim 33, wherein the second image sensor is a photo-multiplier tube (PMT).

65. The phase retardance inspection instrument as recited in claim 33, wherein the neutral beam splitting unit is a neutral beam splitter.

* * * * *